(12) United States Patent
Aravena

(10) Patent No.: US 7,021,934 B2
(45) Date of Patent: Apr. 4, 2006

(54) MULTI-ADJUSTABLE DRILL GUIDE AND FRAMEWORK SYSTEM FOR DENTAL PROSTHETICS

(75) Inventor: Ines Monica Aravena, Camarillo, CA (US)

(73) Assignee: Zimmer Dental, Inc., Carlsbad, CA (US)

( * ) Notice: Subject to any disclaimer, the term of this patent is extended or adjusted under 35 U.S.C. 154(b) by 82 days.

(21) Appl. No.: 10/348,427

(22) Filed: Jan. 21, 2003

(65) Prior Publication Data

US 2004/0142300 A1    Jul. 22, 2004

(51) Int. Cl.
*A61C 8/00* (2006.01)
(52) U.S. Cl. ..................................................... 433/173
(58) Field of Classification Search ................ 433/172, 433/173, 174, 175, 176, 194; 606/54
See application file for complete search history.

(56) References Cited

U.S. PATENT DOCUMENTS

| | | | | |
|---|---|---|---|---|
| 3,748,739 | A * | 7/1973 | Thibert | 433/173 |
| 5,219,286 | A * | 6/1993 | Hader | 433/172 |
| 5,286,196 | A * | 2/1994 | Brajnovic et al. | 433/173 |
| 5,556,278 | A | 9/1996 | Meitner | 433/75 |
| 5,636,986 | A | 6/1997 | Pezeshkian | 433/76 |
| 5,775,900 | A | 7/1998 | Ginsburg et al. | 433/75 |
| 5,876,204 | A | 3/1999 | Day et al. | 433/173 |
| 5,915,962 | A | 6/1999 | Rosenlicht | 433/76 |
| 5,927,982 | A | 7/1999 | Kruger | 433/215 |
| 6,319,000 | B1 * | 11/2001 | Br.ang.nemark | 433/75 |
| 6,692,254 | B1 * | 2/2004 | Kligerman et al. | 433/173 |
| 2003/0108845 | A1 * | 6/2003 | Giovannone et al. | 433/173 |
| 2004/0018469 | A1 * | 1/2004 | Summers | 433/173 |
| 2004/0166476 | A1 * | 8/2004 | Weissman | 433/173 |

OTHER PUBLICATIONS

Brånemark System®, *Fixture Positioning Guides*, 1995, 7 pages.
Bergendal, Birgitta, DDS; Palmqvist, Sigvard, DDS, PhD.; *Laser-Welded Titanium Frameworks for Implant-Supported Fixed Prostheses: A 5-Year Report*, The International Journal of Oral & Maxillofacial Implants, 1999, pp. 69-71.
Naert, I., et al.; *A 5-year Randomized Clinical Trial on the Influence of Splinted and Unsplinted Oral Implants in the Mandibular Overdenture Therapy*, Clinical Oral Implants Research, 1998, pp. 170-177.
Örtorp, Anders, LDS et al.; *Clinical Experiences with Laser-Welded Titanium Frameworks Supported by Implants in the Endentulous Mandible: A 5-Year Follow-up Study*, The International Journal of Prosthodontics, vol. 12, No. 1, 1999, pp. 65-72.

(Continued)

Primary Examiner—Cary E. O'Connor
(74) Attorney, Agent, or Firm—Conley Rose, P.C.

(57) ABSTRACT

In one aspect, a group of inter-connecting, prefabricated components of various shapes and sizes that can be assembled together to form a framework system directly onto dental implants installed in the patient's mouth is disclosed. In another aspect, a group of prefabricated components to form a drill guide system for drilling a properly spaced and oriented implant hole adjacent to another implant hole or adjacent to a fully-installed implant is disclosed. In yet another aspect, improved procedures for installing permanent, implant-supported dental restorations are disclosed, including an immediate loading procedure.

34 Claims, 7 Drawing Sheets

OTHER PUBLICATIONS

Muratori, Giordana, M.D.; *The Gimlet Implant System and Intra-oral Welding*, Journal of Oral Implantology, vol. XV, No. Three, 1989, pp. 194-197.

Rungcharassaeng, Kitichai, DDS, MS; Kan, Joseph Y.K., DDS, MS; *Immediately Loaded Mandibular Implant Bar Overdenture: A Surgical and Prosthodontic Rationale*, The International Journal of Periodontics & Restorative Denistry, vol. 20, No. 1, 2000, pp. 71-81.

Hruska, Arturo, MD; *Welding Implants in the Mouth*, Journal of Oral Implantology, vol. XV, No. Three, 1989, pp. 198-202.

*Fixture Positioning Guides*; Brånemark System; Nobelpharma 1998; PR1 648 95.01.013; (pp. 4).

*Connect™Bar System*: Audax Dental AG; Basel, Switzerland; (pp. 3).

Bergendal, Birgitta, et al; Short Communication: *Laser-Welded Titanium Frameworks for Implant-Supported Fixed Prostheses: A 5 Year Report*: The International Journal of Oral & Maxillofacial Implants; vol. 14, No. 1, 1999; (pp. 69-71).

Naert I, et al; *A 5-year randomized clinical trial on the influence of splinted and unsplinted oral implants in the mandibular overdenture therapy*; Clinical Oral Implant Research 1998: 9: (pp 170-177).

Örtorp, Anders, LDS, et al; *Clinical Experiences with Laser-Welded Titanium Frameworks Supported by Implants in the Endentulous Mandible: A 5-Year Follow-Up Study*; The International Journal of Prosthodontics; vol. 12, No. 1, 1999 (pp. 65-72).

Muratori, Giordano, M.D.: *The Gimlet Implant System and Intra-oral Welding*; Journal of Oral Implantology: vol. XV/No. Three/1989; (pp. 194-197).

Rungcharassaeng. Kitichai, DDS, MS, et al; *Immediately Loaded Mondibular Implant Bar Overdenture: A Surgical and Prosthodontic Rationale*; The International Journal of Peridontics & Restorative Dentistry; vol. 20, No. 1, 2000; (pp. 12).

Hruska, A. R., M.D.; *Welding Implants in the Mouth*; Journal of Oral Implantology, vol. XV/No. Three/1989; (pp. 198-202).

* cited by examiner

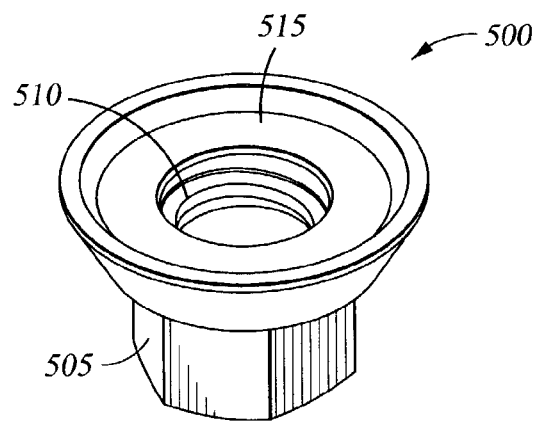
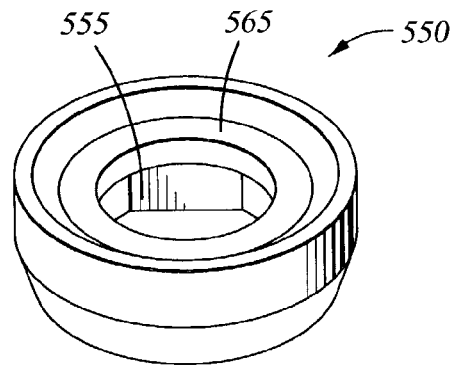
Fig. 9
Fig. 10
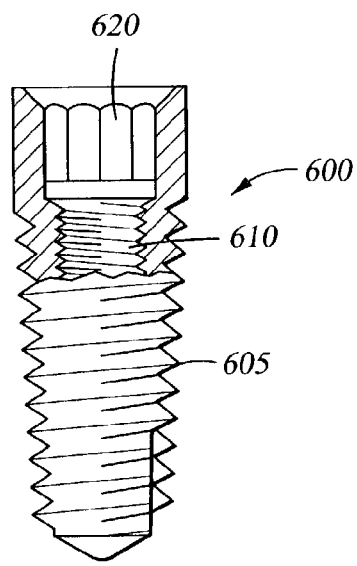
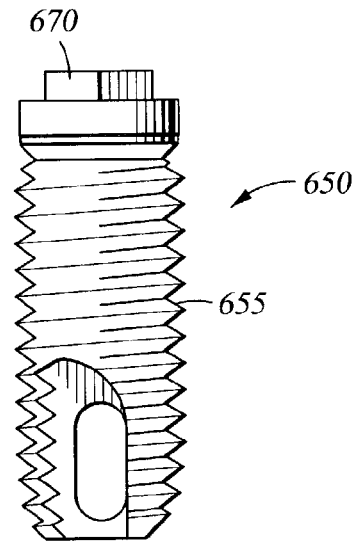
Fig. 11
(PRIOR ART)
Fig. 12
(PRIOR ART)

MULTI-ADJUSTABLE DRILL GUIDE AND FRAMEWORK SYSTEM FOR DENTAL PROSTHETICS

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates generally to dental prosthetics, and more particularly, to intra-oral framework systems and components for implant-supported prosthetic restorations. The invention further relates to methods and apparatus for properly positioning and guiding a drill during dental implant surgery.

2. Description of the Related Art

One of the fastest growing specialties in dentistry is prosthodontics, which is the replacement of missing natural teeth with prosthetic restorations, such as a single tooth, a bridge of several prosthetic teeth, or a denture comprising an arc of prosthetic teeth for an edentulous or partially edentulous patient. The prosthetic restorations are shaped and colored to appear like natural teeth, and are typically supported on dental implants that are surgically secured within the patient's jawbone. Various implant designs are available, such as blades, screws and cylinders, and the implants are generally made of titanium or high titanium alloy.

The conventional surgical procedure for installing one, implant-supported, prosthetic tooth includes drilling a properly positioned hole in the jawbone of the patient, inserting the implant in the hole, and attaching the prosthetic tooth to the implant. In circumstances where two or more implants are installed to support a prosthetic bridge, each implant hole must be angled properly and located the correct distance from adjacent implants and natural teeth to achieve proper alignment and appearance for the prosthetic restoration. Proper implant positioning is also extremely important to ensure that the implant is anchored within sufficient bone structure in the patient's jawbone. Typically, to install an entire upper or lower denture, at least four implant holes are drilled into the upper or lower jawbone.

The most common method for locating a dental implant hole is to visually survey the area and drill the hole in a freehand manner. However, this method can readily result in imperfect bores due to space limitations associated with working inside a patient's mouth. Thus, dental surgeons have encountered difficulty forming implant holes with a sufficient degree of parallelism and proper positioning. A variety of problems can result from flawed or imperfect implant holes, such as uneven force distribution, insufficient bone growth around the implant, secondary infections, and ultimately, implant failure. Therefore, various types of surgical stents and positioning guide systems have been developed to aid the dental surgeon.

A traditional surgical stent is a custom-built template for properly spacing dental implants and for guiding the drill as the implant holes are formed. One exemplary method for making and using a surgical guide stent is described in U.S. Pat. No. 5,556,278 to Meitner, hereby incorporated herein by reference. First, a cast impression is made of the patient's mandible or maxilla jawbone (arch) that includes an edentulous space where one or more implant-supported prosthetic teeth will be installed. A diagnostic tooth set-up formed of wax or other known material is made to fit within the edentulous space of the cast arch. Next, the dental surgeon drills a hole through each diagnostic tooth set-up and into the base of the cast arch. The hole corresponds to the location and orientation of the implant hole in the patient's real arch. Once the hole is drilled in the cast arch, the tooth set-up is removed, a guide post is inserted into each hole, and a guide sleeve is slid over the projecting end of the guide post. A resinous, moldable material is applied on the cast arch around the guide sleeves and cured to form a template. The template with the guide sleeves embedded therein is then removed from the cast arch. When the template is ready for use, the dental surgeon inserts it into the patient's mouth, and the guide sleeves can be radiographically visualized to confirm that they are in the optimum position and orientation before implant holes are drilled therethrough.

Thus, such traditional surgical stents aid the dental surgeon in properly positioning the implant holes, and also guide the drill as the implant holes are being formed. However, because each surgical stent is custom-built, these devices are only useful for a single patient, they are costly to fabricate, and they require a number of intermediary office and laboratory steps to take an impression of the patient's arch and create a cast model from which the surgical stent is formed.

Therefore, to reduce costs and the number of steps associated with fabricating a traditional surgical stent, various forms of prefabricated surgical stents have been developed. One exemplary prefabricated surgical stent is disclosed in U.S. Pat. No. 5,775,900 to Ginsberg et al., hereby incorporated herein by reference, which describes a clear, thermoplastic acrylic resin stent to facilitate visualization of the underlying supporting tissues. A kit is provided to the dental surgeon comprising prefabricated stents of mandibular and/or maxillary arches in small, medium, and large base sizes based on anatomical averages for the population with various tooth arrangements on each base size. For any particular patient, a stent of the appropriate base size is selected and placed in water of 120°–160° F. for approximately 2 minutes, allowing the resin to become moldable. The inner surface of the stent is then molded in the mouth of the patient or on a cast model of the patient's arch to closely approximate the edentulous ridge. Simultaneously, the outer surface of the stent is adjusted to position the prosthetic teeth. Once formed and subsequently cooled, the stent becomes stable and can be placed in the patient's mouth at the time of implant surgery for proper alignment of the implants. Thus prefabricated stents provide some advantages over traditional surgical stents. However, each prefabricated stent is only useful for a single patient.

In addition to surgical stents, prefabricated drill guide systems have been developed. One exemplary drill guide system is disclosed in U.S. Pat. No. 5,636,986 to Pezeshkian, hereby incorporated herein by reference. Pezeshkian describes prefabricated drill guide fixtures comprising interconnected housings configured in the shape of teeth with vertically disposed drill bushings passing therethrough. The drill guide fixtures are provided in different configurations depending on the number of prosthetic teeth that will be installed. For example, a drill guide fixture may comprise three housings fixed together in a size and configuration to resemble three adjacent prosthetic teeth that will be installed as a bridge. A pin is used to position the fixture in an initially drilled hole, and the fixture is rotated about the axis of the pin until the tooth-shaped housings are properly aligned. The dental surgeon then drills through the drill bushings in each housing to form the implant holes. The drill bushings guide the drill and reduce the likelihood of slippage or breakage of the drill bit during drilling. Although the drill guide fixtures are prefabricated and may theoretically be used more than once, dental restorations come in a great variety of configurations. Therefore, the dental surgeon would likely be required to purchase a separate drill guide fixture for each patient to provide the configuration that matches the patient's restoration requirements.

Another exemplary drill guide system is disclosed in U.S. Pat. No. 5,915,962 to Rosenlicht, hereby incorporated herein by reference. Rosenlicht describes a kit comprising a plurality of tooth emulations that differ in size and shape to replicate cuspids, bicuspids, molars, etc. Each tooth emulation includes a pilot guide hole extending along an axis of rotation. The tooth emulations are connected together in an articulated manner for relative movement and relative axial orientation to each other. The dental surgeon connects together a plurality of tooth emulations to form an articulatable model approximating the size and shape of the patient's natural teeth. The model is positioned on the patient's edentulous site, or a cast model thereof, and adjusted as necessary. Then the model is luted or otherwise rigidified to form a rigid guide for drilling implant holes into the patient's jawbone through the pilot guide hole in each emulation. Thus, this drill guide system includes prefabricated tooth emulations that are intended to enable the dental surgeon to build a model that matches the patient's restoration configuration. However, each articulatable model is only useful for one patient.

An alternate type of guide is a drill positioning guide. One exemplary type of drill positioning guide is the Brånemark System offered by Nobelpharma AB. This system includes stainless steel, L-shaped guides, each comprising a vertical pin portion and a horizontal positioning portion. For each guide, the pin has a particular diameter and the positioning portion has a particular lateral length. Once the first implant hole is drilled, the pin is placed inside the hole such that the positioning portion extends horizontally over the gumline to locate the next implant hole. The drill bit is aligned against the end of the positioning portion opposite the pin to drill the adjacent implant hole. Therefore, the lateral length of the positioning portion determines the centerline to centerline distance between adjacent implants to ensure adequate spacing between implants. Further, the height of the positioning portion provides a guide for drilling the depth of the implant hole. In particular, the positioning portion is 8 mm high, and may include notches to indicate each 2 mm increment. The dental surgeon can align depth indicators on the drill bit with either the full height of the positioning portion or the notches on the positioning portion to drill implant holes of approximately equal depth.

Accordingly, the L-shaped-prefabricated positioning pins facilitate spacing between implants and enable the drilling of implant holes having approximately equal depth. These positioning guides may be used more than once for any patient with any restoration configuration. However, these pins do not guide the drill bit to ensure that it remains oriented at the proper angle to drill implant holes having a sufficient degree of parallelism. Therefore, it would be desirable to provide a drill guide system comprising simple, prefabricated components that may be used more than once, for any restoration configuration, that enable precise implant spacing, and also ensure that the implant holes are drilled at the proper angle and orientation.

Employing widely used conventional techniques, once the implants are positioned, they perform no function for one to six months to allow time for the implants to osseointegrate into the patient's jawbone. During this time, the patient wears a temporary, removable denture. Once the osseointegration period is complete, the next step in providing a permanent, multi-unit restoration is to create a framework that is typically custom-fabricated in a laboratory for the individual patient from gold alloy or titanium components. The framework interconnects and joins together the implants, provides a foundation for the prosthetic restoration, and provides an attachment structure for connecting the prosthetic bridge or denture to the multiple implants. Thus, the framework is a permanent structure disposed between the implants and the dental restoration.

The process for creating a custom-fabricated framework is similar to the process for creating a traditional surgical stent. First, a cast impression of the patient's mandible or maxilla jawbone (arch) is taken in the dentist's office, from which a model of the patient's arch is made to indicate the locations of the implants. Using the model, the entire framework is fabricated in a laboratory to precisely fit onto the implants. The prefabricated framework is then transferred to the dental surgeon for positioning onto the actual implants. Although formed using the model, the prefabricated framework may not precisely fit onto the implants, in which case the framework must be adjusted. The adjustment may require that a bar be cut and re-soldered or re-cast, which often must be performed in a laboratory that is located elsewhere. If a minor change is required, the dental surgeon can adjust the framework in the office, but these modifications are typically finalized in the off-premises laboratory. This fitting and adjustment process may go back and forth between the laboratory and the surgeon's office a number of times, thereby increasing the cost, time, and inconvenience to the patient.

Another type of framework system is the laser-welded titanium framework, which does not require laboratory involvement and may be installed as an integral part of the implant surgery to immobilize the implants. The laser-welded framework system allows a dental surgeon to custom build the titanium framework right into the patient's mouth by welding together titanium components using an intra-oral welding machine. Since the framework is built onto the implants in the patient's mouth, a good fit can be ensured. However, the skill required to weld intra-orally limits the widespread application of this type of framework system. Accordingly, it would be desirable to provide a framework system that can be constructed directly onto the actual implants without requiring special skills, such as intra-oral welding.

Audax Dental AG of Basel, Switzerland offers the Connect Bar System comprising a variety of components designed to be positioned to form a framework system in the dentist's office without intra-oral welding. Specifically, the Connect Bar System comprises a Housing Unit, a Bar Unit, and a Bar Sleeve. The Housing Unit includes a bore for receiving a fixation screw, a double-hex (12-sided) recess formed in the base for receiving a hexagonal extension from a non-rotating abutment, and one or two sockets formed into the sides, each socket for receiving a ball head of a Bar Unit. The Bar Unit comprises a straight portion and a ball head formed on one end that is designed to fit into the socket of the Housing Unit. The Bar Sleeve comprises a sleeve designed to fit over the straight portions of two adjacent Bar Units when their straight portions are aligned, end-to-end.

To assemble the Connect Bar System, non-rotational abutments with hexagonal upper extensions are first fit onto the implants. A Housing Unit is then disposed on top of each abutment so that the double-hex recess of the Housing Unit receives the hexagonal upper extension of the abutment, thereby enabling the Housing Unit to be adjusted to one of twelve rotational positions with respect to the implant. A Bar Unit is connected to each Housing Unit by inserting the ball head portion into a socket of the Housing Unit, thereby allowing full rotational movement of the Bar Unit with respect to the Housing Unit. Prior to installation, the Bar Units are cut to the appropriate length as perceived by the dental surgeon. To join adjacent Bar Units and complete a bar assembly that spans between Housing Units, the Bar Sleeve is fit over the ends of adjacent Bar Units.

Thus, the Connect Bar System offers the advantages of providing a framework system consisting of components that may be assembled together and installed directly into the patient's mouth without requiring intra-oral welding. However, the dental surgeon is required to precisely cut the Bar Units to the proper length, which adds to the time required to perform the procedure. Also, three components, namely two Bar Units and a Bar Sleeve, must be interrelated and assembled to form a single bar assembly to span between two Housing Units, thereby adding to the cost and the number of components required for the framework system. Further, the Housing Unit does not connect directly to the implant but instead connects to an intermediary non-rotational abutment, thereby adding another component to the overall prosthetic system. Additionally, the Housing Unit is restricted to one of twelve distinct rotational positions (30° apart) with respect to the implant, rather than having full rotational freedom of movement. Accordingly, it would be desirable to provide a simplified framework system of prefabricated components that did not require adjustment by the dental surgeon, that had full rotational freedom of movement with respect to the implant to maximize adjustability during installation, and that enabled direct connection to the implants to reduce the total number of components in the final restoration.

The present invention overcomes various of the deficiencies of the prior art.

BRIEF SUMMARY OF THE PREFERRED EMBODIMENTS

The preferred embodiments of the present invention feature a system of components that may be configured to form a framework system for implant-supported, permanent dental restorations, and a method of constructing a dental framework system directly onto implants in the patient's mouth. Certain preferred embodiments feature a system of components that may be configured to form a drill guide system, and a method of drilling dental implant holes that are properly spaced and aligned.

In one preferred embodiment, the system comprises modular collars and connective stem members for forming a framework system. The modular collars preferably include a bore for receiving a fixation screw for connection to an implant and preferably two side sockets that may include bushings for receiving end portions of the connective stem members. The modular collars optionally include a top recess for receiving an attachment portion of the prosthetic restoration. The modular collars may be one-piece or two-piece components, and may be provided in a variety of shapes. The connective members preferably include a bar portion or an elbow portion with enlarged portions on each end that are preferably spherical. The modular collars and connective members are preferably separate components that interconnect to form a supporting framework for a dental prosthesis. In one respect, the collars serve as connective nodes for connection to other such nodes via the connective stems. Alternatively, a one-piece span member comprising a bar portion and collar end portions on each end formed into a unitized member may be provided for joining two adjacent implants to support a bridge. These components permit a dental surgeon to fabricate and install the appropriate supportive framework in the same surgical setting in which the implants are surgically implanted, and to create the framework from prefabricated, premeasured components so as to provide a properly fitting and aesthetically pleasing dental restoration with reduced time, cost, and complexity.

In another preferred embodiment, the system comprises a positioning assembly, a connective member, and a drill sleeve for forming a drill guide system. The positioning assembly preferably comprises a positioning sleeve and paralleling pin. The positioning sleeve includes a bore for receiving the paralleling pin and a channel with a narrowed entrance for receiving one end portion of a connective member. Alternatively, the positioning assembly comprises an implant with a modular collar attached thereto. The drill sleeve preferably includes a bore for receiving a drill bit and a channel for receiving another end portion of the connective member that extends between the positioning sleeve or the implant with the modular collar connected thereto and the drill sleeve. The drill guide systems permit the dental surgeon, with great precision, to drill holes and install implants in the optimum position and with the appropriate orientation, such as parallel to a previously installed implant.

Thus, the preferred embodiments of the present invention comprise a combination of features and advantages that overcome various problems of prior apparatus and methods. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiments of the present invention, reference will now be made to the accompanying drawings, where like components have like reference numerals and wherein:

FIG. 9 is an isometric top and side view of one embodiment of an interface conversion piece that connects with a two-stage implant to extend the implant above the gumline;

FIG. 10 is an isometric top and side view of another embodiment of an interface conversion piece;

FIG. 11 is an isometric side view, partially in cross-section, of an exemplary two-stage implant that connects with the interface conversion piece of FIG. 9;

FIG. 12 is an isometric side view, partially in cross-section, of another exemplary two-stage implant that connects with the interface conversion piece of FIG. 10;

DETAILED DESCRIPTION OF THE PREFERRED EMBODIMENTS

In one aspect, the preferred embodiments of the present invention comprise a plurality of components that may be assembled to form a dental framework for supporting and attaching a permanent, implant-supported, prosthetic restoration. Titanium is the preferred material for the framework components. However, the components could also be formed of gold or any other material that is strong and compatible with living tissue.

Figure 1:
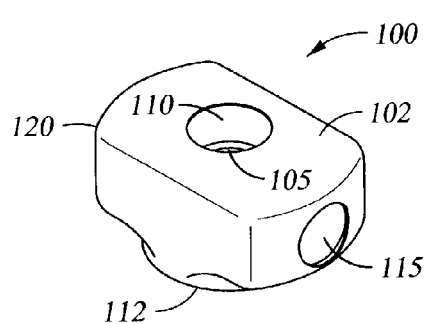
FIG. 1 is an isometric side and top view of one embodiment of a prefabricated modular collar having a rectangular shape.
Figure 2:
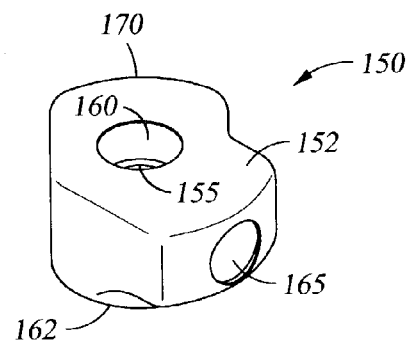
FIG. 2 is an isometric side and top view of another embodiment of a pre-fabricated modular collar having an angled shape.

Referring to FIGS. 1–4, preferred embodiments of the framework components preferably comprise modular collars of various configurations, such as the collar 100 of FIG. 1, which may be rectangular, for example, and the angled collar 150 of FIG. 2. Preferred embodiments of the framework components preferably further comprise connective members of various shapes and sizes, such as the connective stems 200 of FIG. 3, and the connective elbow 250 of FIG. 4.

FIG. 1 and FIG. 2 depict preferred configurations of modular collars 100, 150, respectively, each comprising a preferably titanium body 102, 152 with a bore 105, 155 extending axially therethrough for receiving a fixation screw, an optional top recess 110, 160 for receiving an attachment portion of a prosthetic restoration, preferably two side sockets 115, 120 and 165, 170 for joining with connective members, and a lower extension 112, 162 designed to engage the top of the implant. Rather than lower extensions 112, 162, the collars 100, 150 may alternatively include lower recesses designed to receive an extension from the top of an alternative implant.

Figure 15:
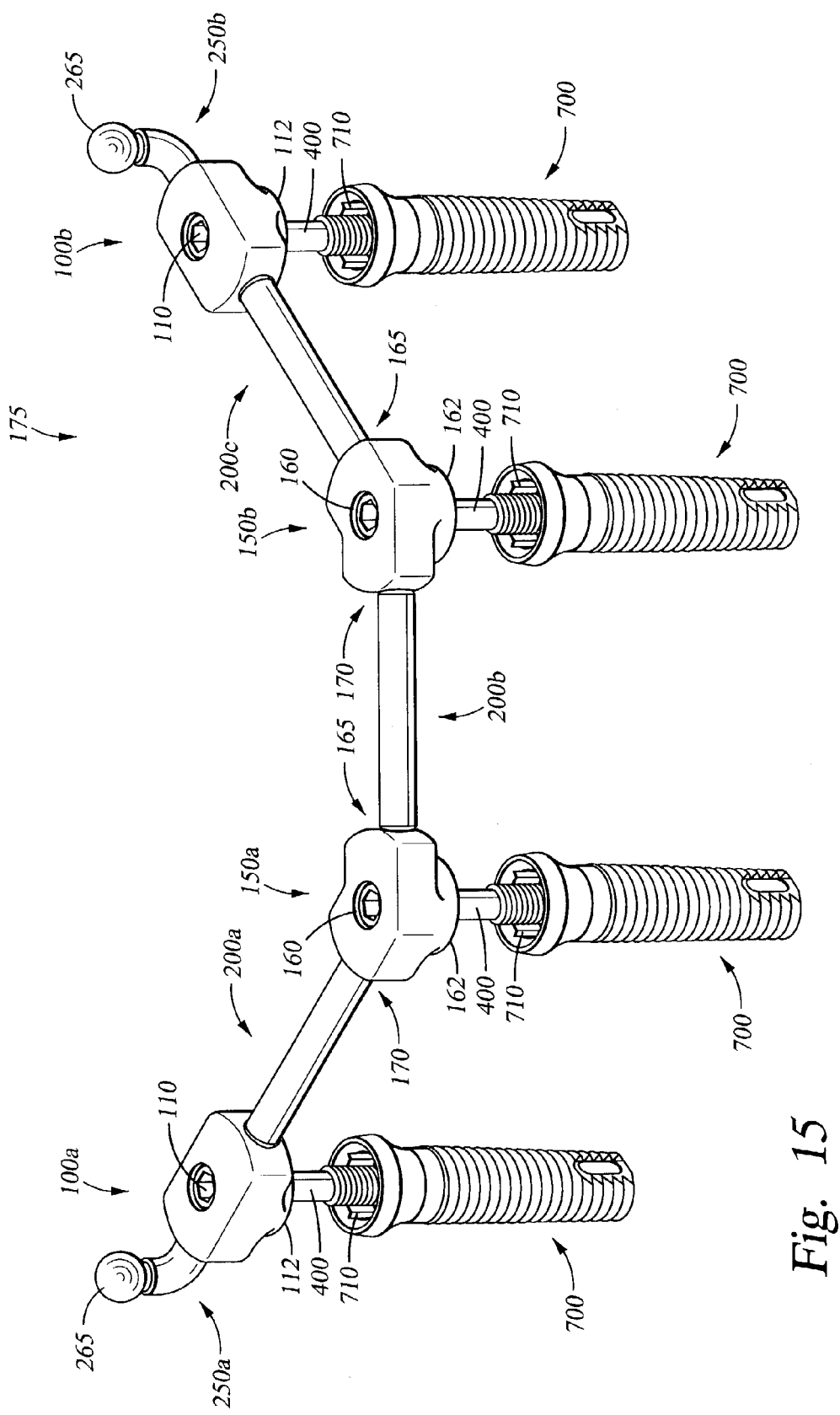
FIG. 15 is an isometric view of one embodiment of an assembled framework system connected to implants for supporting a complete lower prosthetic arch.
Figure 16:
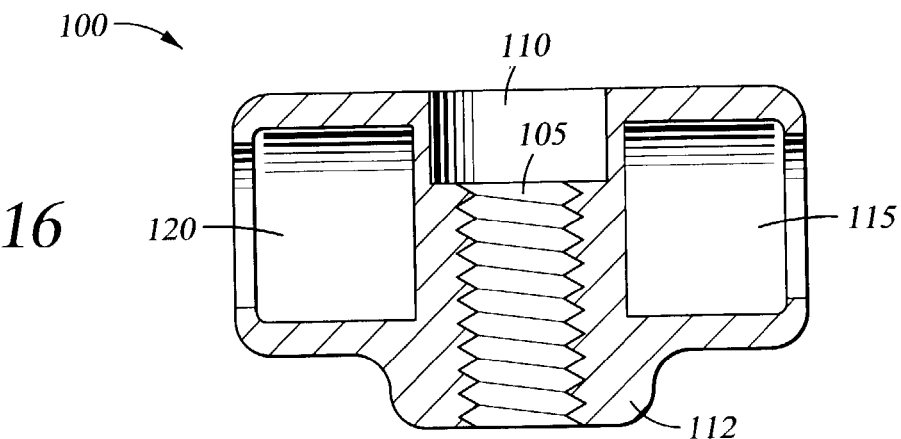
FIG. 16 is a cross-sectional side view of the pre-fabricated modular collar of FIG. 1.

In more detail, FIG. 16 depicts a cross-sectional side view of collar 100, showing side sockets 115, 120 having a preferably cylindrical cross-section. As understood with reference to FIGS. 1 and 16, sockets 115, 120 of collar 100 are coaxially aligned. By contrast, and referring momentarily to FIGS. 2 and 15, sockets 165, 170 of angled collars 150 are oriented such that they lie in the same plane but are skewed with respect to one another to intersect within bore 160 at a predetermined angle, such as at an angle of between 100 and 170 degrees. In one preferred embodiment, the angle of intersection of the socket axis for collar 150 is 135 degrees.

Figure 3:
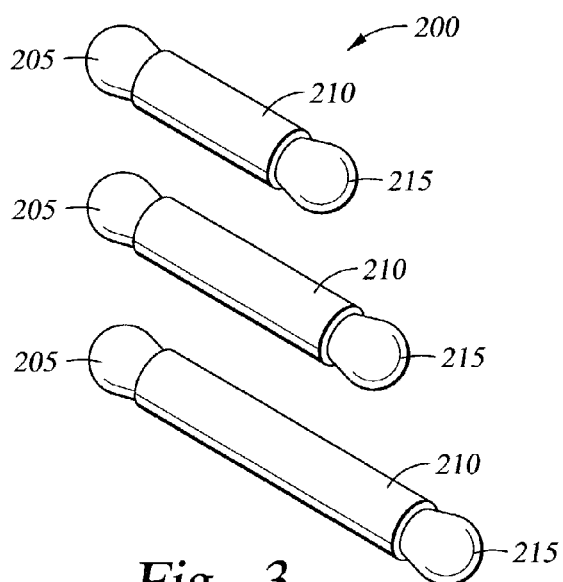
FIG. 3 is an isometric view of three representative connective stems of varying lengths.
Figure 4:
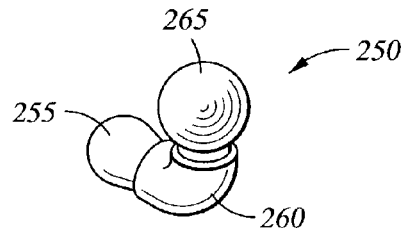
FIG. 4 is an isometric view of an exemplary connective elbow.

As shown in FIG. 3, the preferably titanium connective stems 200 are elongate members that each preferably include a bar portion 210 of a particular length having two enlarged end portions 205, 215 that are preferably spherically shaped and adapted to fit within the side sockets 115, 120 and 165, 170 of the collars 100, 150, for example. FIG. 4 depicts an alternative connective elbow 250 for placement at the ends of the framework comprising an elbow portion 260, an enlarged end portion 255 that is preferably spherically shaped for connecting to a collar 100, 150, and a preferably spherically shaped rounded attachment portion 265 for connecting to the prosthetic restoration. The length and diameter of bar portions 210 of stems 200 and portion 260 of elbow connector 250 may be any suitable dimension. Certain preferred lengths for connective stems 200 are approximately 8 millimeters (mm), 10 mm and 12 mm measured end-to-end and, having such lengths, are approximately 2 mm in diameter measured across the bar portion 210. The spherical radius of end portions 205, 215 may be, for example, approximately 1 mm.

Figure 19:
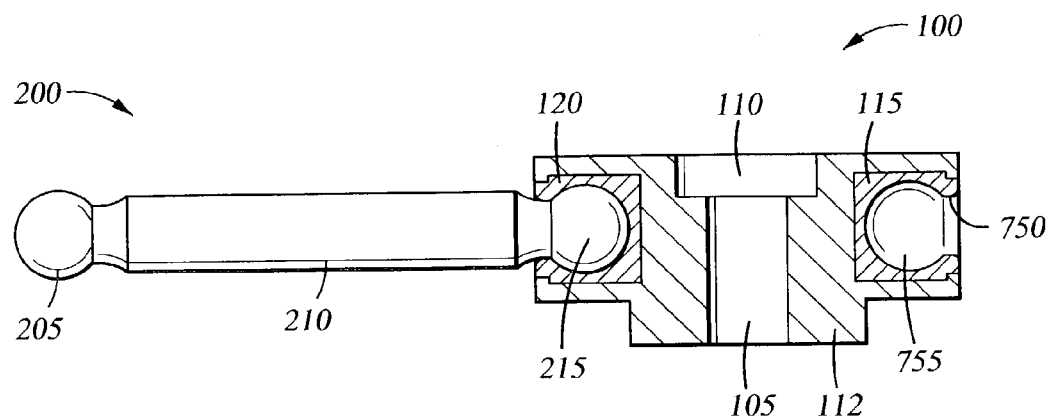
FIG. 19 is a cross-sectional side view of the pre-fabricated modular collar of FIG. 1 with rounded bushings disposed within each side socket and a connective stem connected thereto.
Figure 20:
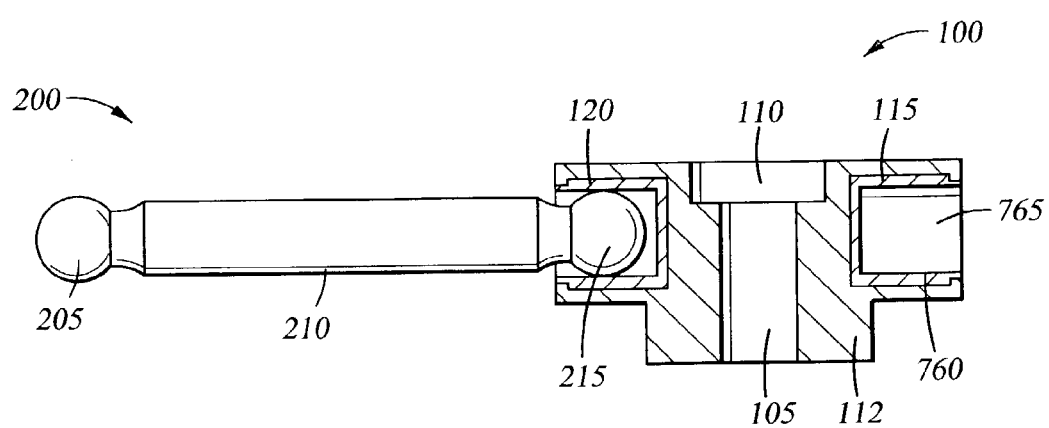
FIG. 20 is a cross-sectional side view of the prefabricated modular collar of FIG. 1 with cylindrical bushings disposed within each side socket and a connective stem connected thereto.

FIG. 15 provides an isometric view of one exemplary, fully-assembled framework system 175 comprising collars 100, 150, connective stems 200, and connective elbows 250 for supporting and attaching a full prosthetic lower arch. The modular collars 100, 150 connect via fixation screws 400 to the implants 700. Further, the modular collars 100, 150 connect to one another via connective stems 200 such that the bar portions 210 of the connective stems 200 span the space therebetween. In preferred embodiments, a bushing is disposed within each of the sockets 115, 120 and 165, 170 of the one-piece collars 100, 150 to receive the end portions 205, 215 of the connective stems 200, thereby providing a friction fit between the connective stems 200 and the collars 100, 150. In more detail, FIG. 19 depicts a cross-sectional side view of an exemplary one-piece collar 100 with a bushing 750 disposed in each of the side sockets 115, 120, the bushing 750 having a spherical recess 755. The bushings 750 are preferably press-fit into the side sockets 115, 120, and the end portions 205, 215 of the connective stems 200 preferably snap tightly into the spherical recesses 755. Similarly, FIG. 20 depicts a cross-sectional side view of the exemplary one-piece collar 100 with an alternative bushing 760 disposed in each of the side sockets 115, 120, the alternative bushing 760 having a cylindrical recess 765.

Both types of bushings 750, 760 provide a friction-fit to prevent angular and rotational movement of the connective stems 200 with respect to the collars 100, 150. However, the cylindrical recess 765 of the alternative bushing 760 is preferably dimensioned to enable a length adjustment of the connective stems 200 by approximately 1 mm, for example. Referring to FIG. 15, if a connective stem 200a of 7 mm end-to-end length is required to connect between collar 100a and collar 150a, then a connective stem 200a of 8 mm may be utilized if at least one of the sockets 105, 170 includes an alternative bushing 760 with a cylindrical recess 765 that enables a 1 mm lengthwise adjustment. Further, a connective stem 200a of 9 mm may be utilized if both of the sockets 105, 170 include a bushing 760 that enables a 1 mm lengthwise adjustment.

As understood with reference to FIG. 15, collars 100, 150 serve as connective nodes that tie together other components of the framework system 175. For example, angled collar 150a serves as a connective node by interconnecting collars 100a and 150b via stems 200a, 200b. As a further example, collar 100b serves as a connective node by interconnecting collar 150b and elbow 250b via its connection with stem 200c. As described more fully below, framework 175, once assembled and installed on implants 700, creates a supporting system for a dental prosthesis, where the system is constructed from prefabricated and presized components to satisfy the unique requirements of the particular patient. The non-angled modular collars 100 are preferably connected to implants 700 toward the back of the arch, while the angled collars 150 are preferably connected to implants in the front of the arch. Further, connective elbows 250 are preferably provided at the very back of the arch on each side. In order to depict how the implants 700 and collars 100, 150 fit together, the collars 100, 150 are shown displaced from the implants 700. However, when the framework system 175 is installed, the fixation screws 400 will be fully threaded into the implants 700, thereby causing the lower portions 112, 162 of collars 100, 150 to fit into the upper recesses 710 of the implants 700 such that the collars 100, 150 are mounted directly atop the implants 700.

Figure 5:
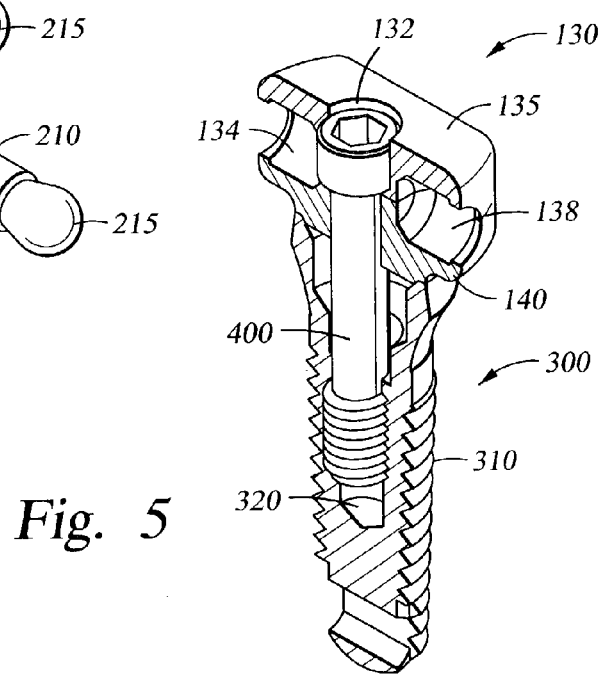
FIG. 5 is an isometric view, partially in cross-section, of another embodiment of a pre-fabricated collar connected to an implant via a fixation screw, the collar being formed of two sections.
Figure 17:
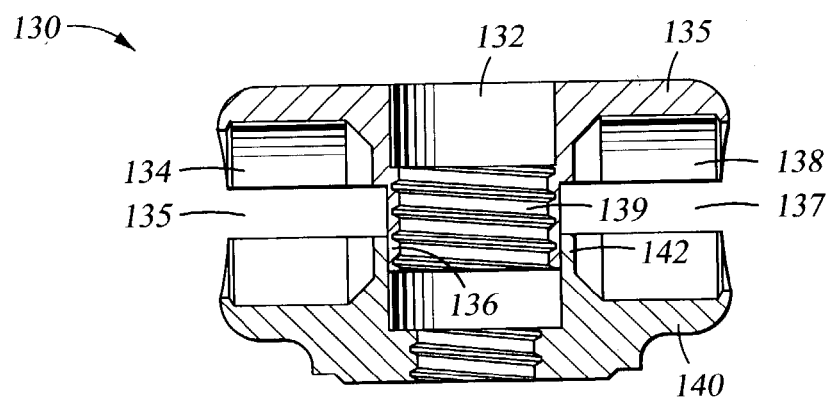
FIG. 17 is a cross-sectional side view of the two interconnected sections forming the pre-fabricated collar of FIG. 5.

Various alternate embodiments of framework components may be provided. FIGS. 5 and 17 depict an alternate two-piece, split collar 130, which may be utilized instead of the one-piece modular collars 100, 150. FIG. 5 is an isometric view, partially in cross-section, of the two-piece collar 130 connected to an implant 300 via a fixation screw 400, and FIG. 17 depicts the two-piece collar 130 in a side, cross-sectional view. The two-piece collar 130 comprises an upper section 135 and a lower section 140 that preferably interconnect via a tab 136 extending downwardly from the upper section 135 into a tab 142 extending upwardly from the lower section 140, thereby creating an interference fit. The two-piece collar 130 includes an axial bore 132, that preferably includes internal threads 139, extending through both sections 135, 140 for receiving the fixation screw 400, and preferably two side sockets 134, 138 formed when the upper and lower sections 135, 140 are inter-locked together. The internal threads 139 in the axial bore 132 are provided to enable disengagement of the two sections 135, 140 via the jackscrew method. Before the collar 130 is connected to the implant 300, the upper and lower sections 135, 140 are slightly separated as shown in FIG. 17, thereby forming gaps 133, 137 in the side sockets 134, 138. This separation provides adequate space for the end portions 205, 215 of a connective stem 200 to engage the side sockets 134, 138 while the position of the connective stem 200 is being adjusted.

Once the angle and orientation of the connective stem 200 is set, the upper and lower sections 135, 140 of the two-piece collar 130 are press-fit together around an end portion 205, 215 of the connective stem 200 by tightening the fixation screw 400 through the collar 130. As shown in FIG. 5, the two-piece collar 130 connects to an implant 300 having a threaded axial bore 320 for receiving the fixation screw 400. The screw 400 is tightened to a specified torque to compress the end portion 205, 215 of the connective stem 200, thereby preventing the stem 200 from rotating with respect to the two-piece collar 130. The implant 300 further includes external threads 310 that anchor to bone in the patient's jaw when the implant 300 is installed.

Figure 6:
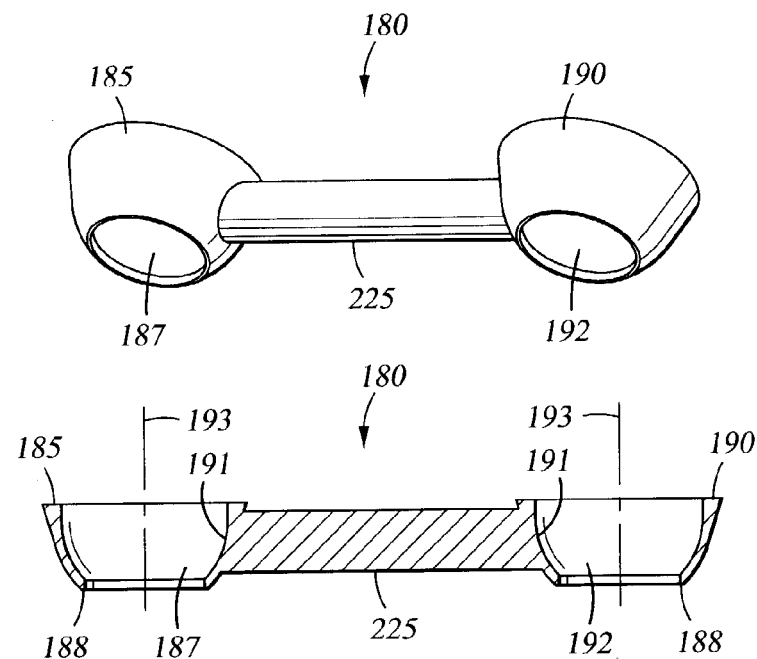
FIG. 6 is an isometric side and bottom view of a one-piece span member.
Figure 7:
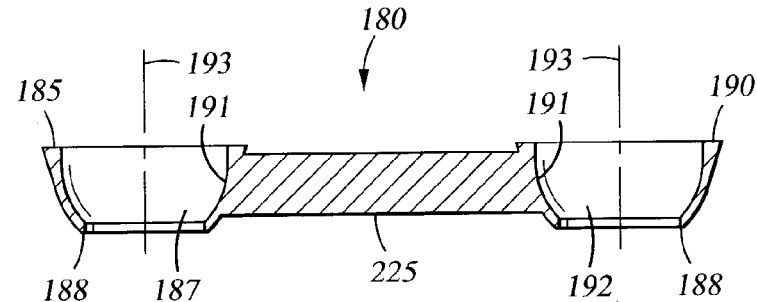
FIG. 7 is a cross-sectional side view of the span member of FIG. 6.
Figure 8:
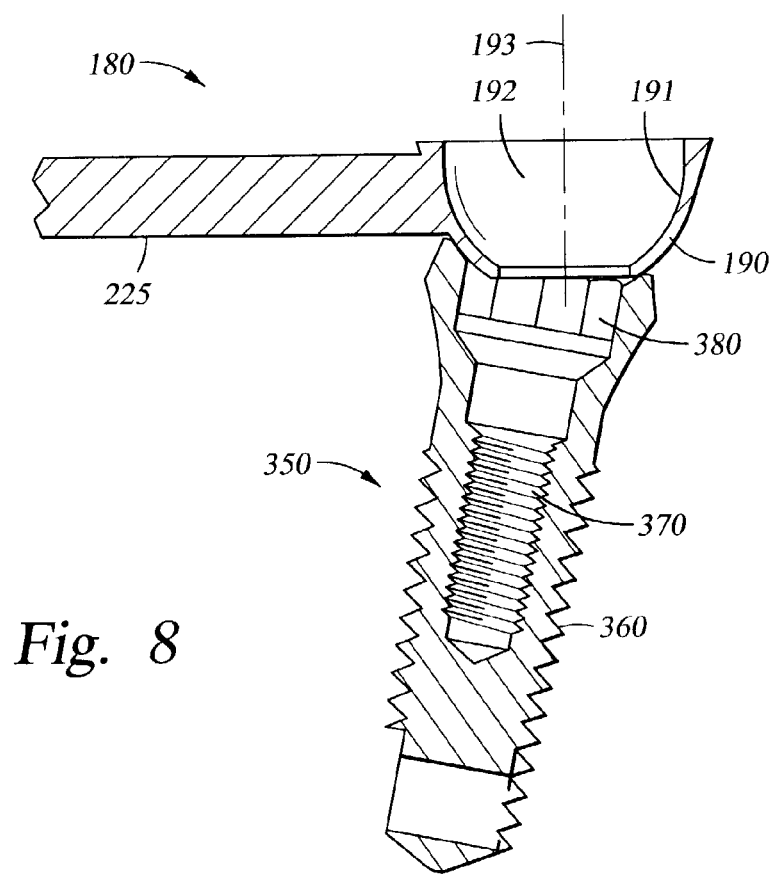
FIG. 8 is a cross-sectional side view of one end of the span member of FIG. 6 connected to an implant disposed at an angle.

In still another embodiment, shown in isometric view in FIG. 6 and in cross-sectional side view in FIG. 7, a one-piece span member 180 may be provided to connect between adjacent implants. The one-piece span member 180 is utilized with a bridge restoration supported by only two implants. The span member 180 comprises a bar portion 225 and two collar ends 185, 190, each having an axial bored area 187, 192. Bored areas 187, 192 include inwardly tapered surfaces 191 and a central axis 193. FIG. 8 depicts one end of the span member 180 connected to an implant 350 disposed at an angle relative to the central axis 193 of collar end 190. The implant 350 includes external threads 360, an internal threaded bore 370 for receiving a fixation screw (not shown), and an internal hexagonal recess 380. The collar ends 185, 190 and the bar portion 225 of the span member 180 are integrated into one unitized component, and the collar ends 185, 190 are preferably sized and configured so that portions 188 of the collar ends 185, 190 extend into the recess 380 of the implant 350 and enable rotational movement with respect to the implant 350. Preferably, portions 188 of collar ends 185, 190 are generally spherical in shape. The axial bored areas 187, 192 are each adapted to accept a fixation screw to secure the span member 180 to the implant 350. The bridge restoration connects to the implant 350 by snapping into place on the bar portion 225 of the span member 180. It is preferred that bored areas 187, 192 have a diameter substantially greater than the diameter of the fixation screw used to attach span member 180 to implants 350 so as to be employable with implants that are disposed at an angle relative to the axis of collar end 185, 190, as shown in FIG. 8.

Each of the preferred embodiments of the framework collars described above is designed to connect directly onto an implant that extends above the gumline. However, the dental surgeon may utilize two-stage implants comprising a first stage that stops below the gumline and a second stage that connects to the first stage and extends above the gumline. Thus, additional preferred embodiments of the framework components comprise interface conversion pieces of various configurations, such as pieces 500, 550 of FIG. 9 and FIG. 10, respectively. Conversion pieces 500, 550 connect to the first stage of a two-stage implant and extend above the gumline such that collars 100, 150, 130 and span member 180 can connect thereto. In one embodiment, the conversion piece 500 of FIG. 9 includes a hexagonal extension 505, a threaded axial throughbore 510, and an upper recessed portion 515. In another embodiment, the conversion piece 550 of FIG. 10 comprises a multi-sided recess 555 and an upper recessed portion 565.

FIG. 11 depicts the first implant stage 600 of one exemplary, prior art, two-stage implant having external threads 605, a threaded axial bore 610 for receiving a fixation screw (not shown), and a hexagonal recess 620. The conversion piece 500 of FIG. 9 can be utilized in place of a conventional second stage to extend the first implant stage 600 of FIG. 11 above the gumline by fitting the hexagonal extension 505 of the conversion piece 500 into the hexagonal recess 620. Then the lower portions of the modular collars, such as, for example, the lower portions 112, 162 of collars 100, 150 of FIGS. 1 and 2, respectively, fit into the upper recessed portion 515 of the conversion piece 500, and a fixation screw (not shown) is threaded through the collar 100 or 150, the conversion piece 500, and into the first implant stage 600. Thus, the conversion piece 500 enables the preferred embodiments of the framework components, such as collars 100, 150, to be utilized with two-stage implants.

FIG. 12 depicts a first implant stage 650 of another exemplary, prior art, two-stage implant having external threads 655, an internal threaded bore (not shown), and a hexagonal extension 670. The conversion piece 550 of FIG. 10 is utilized to extend the first implant stage 650 above the gumline by fitting the hexagonal extension 670 of the first implant stage 650 into the multi-sided recess 555 of the conversion piece 550. The lower portions 112, 162 of the modular collars 100, 150 shown in FIGS. 1–2, for example, fit into the upper recessed portion 565 of the conversion piece 550, and a fixation screw (not shown) extends through the collar 100 or 150, the conversion piece 550, and into the first implant stage 650. Accordingly, interface conversion pieces, such as conversion pieces 500, 550 of FIGS. 9 and 10, respectively, would only be utilized with the first implant stage of two-stage implants, such as first implant stages 600 and 650 that stop below the gumline. The conversion pieces, such as pieces 500 and 550, act to extend the first implant stages 600 and 650 above the gumline so that the framework components can be attached thereto.

Figure 13:
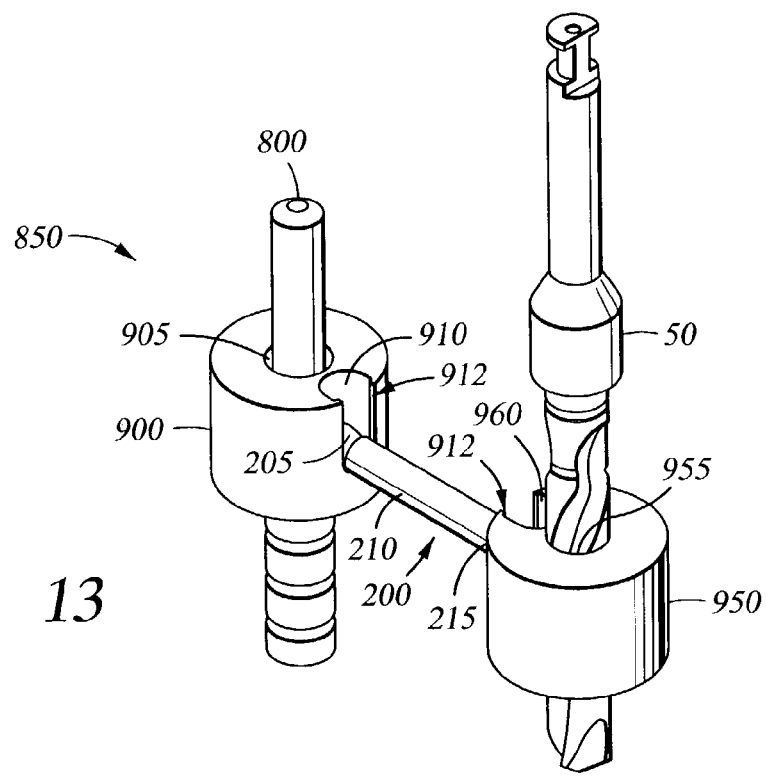
FIG. 13 is an isometric side view of one embodiment of interconnected components forming a preferred drill guide system.
Figure 14:
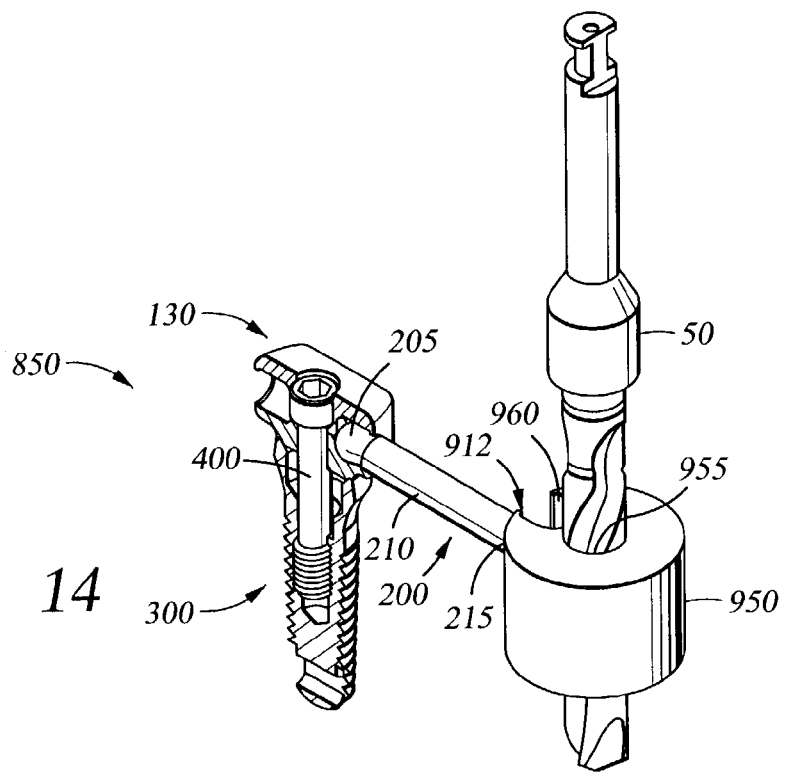
FIG. 14 is an isometric side view, partially in cross-section, of another embodiment of interconnected components forming another preferred drill guide system.
Figure 18:
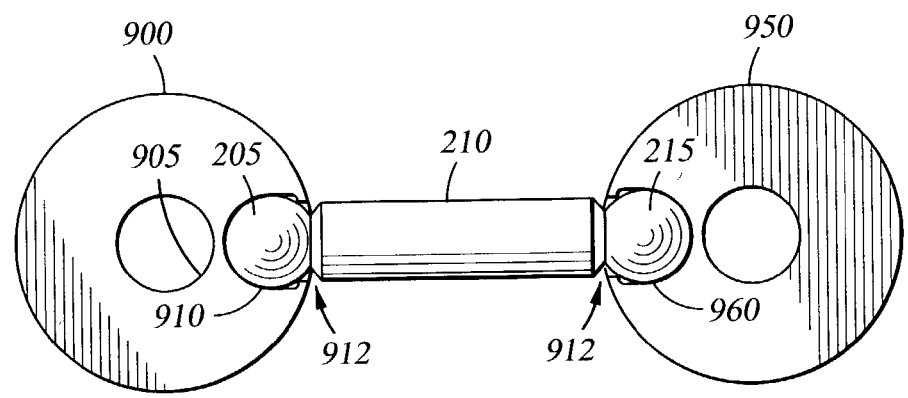
FIG. 18 is a top view of the drill guide system shown in FIG. 13, with the paralleling pin and drill not shown for clarity.

In another aspect, the preferred embodiments of the present invention comprise a plurality of components that may be assembled to form a drill guide system for drilling properly spaced and aligned dental implant holes for multi-unit prosthetic restorations. FIG. 13 and FIG. 14 depict the components of two preferred embodiments, respectively, of a drill guide system connected together. The drill guide systems of FIGS. 13–14 each comprise a positioning assembly 850, a connective stem 200, and a drill sleeve 950. As shown in FIGS. 13 and 18, one embodiment of the positioning assembly 850 comprises a paralleling pin 800 and a positioning sleeve 900. The positioning sleeve 900 preferably includes a throughbore 905 for receiving the paralleling pin 800 and a channel 910 for receiving the end portion 205 of the connective stem 200. The drill sleeve 950 preferably includes a throughbore 955 for receiving a drill bit 50 and a channel 960 for receiving the opposing end portion 215 of the connective stem 200, thereby joining the drill sleeve 950 to the positioning sleeve 900 via bar portion 210. Channel 910 and channel 960 each have a narrowed opening 912. Openings 912 are wider than the diameter of bar portion 210 of stem 200 but smaller in width than the diameter of spherical ends 205, 215. In this manner, channels 910, 960 and their respective narrow entrance or opening 912, form a capture for receiving and securing ends 205, 215 of stem 200.

To utilize the drill guide system of FIGS. 13 and 18, a first implant hole is drilled using conventional techniques, and the paralleling pin 800 is then placed through the positioning sleeve 900 to extend into the first implant hole. A connective stem 200 with a bar portion 210 of the appropriate length to provide the desired center-to-center spacing between implants is then selected by the dental surgeon. The end portion 205 of the connective stem 200 is slid downwardly in the channel 910 of the positioning sleeve 900, and the opposing end portion 215 is slid downwardly in the channel 960 of the drill sleeve 950, thereby joining the two sleeves 900, 950 as ends 205, 210 are captured within channels 910, 960. A drill bit 50 is then placed through the bore 955 of the drill sleeve 950, and a second implant hole is drilled therethrough. Accordingly, the connective stem 200 locates the drill sleeve 950 through which the drill bit 50 drills the second implant hole. The length of the drill sleeve 950 is sufficiently long to guide the drill bit 50 and prevent the drill bit 50 from drilling off angle, ensuring that the second implant hole is drilled parallel to the first. In like manner, all other implant holes are drilled at the proper distance and orientation, so that a framework system such as that shown in FIG. 15 can be constructed.

An alternative embodiment of the positioning assembly 850 comprises replacing the paralleling pin 800 and positioning sleeve 900 of FIG. 13 with a fully-installed first implant having a modular collar attached thereto. FIG. 14 depicts an exemplary configuration of the alternative positioning assembly 850 comprising the implant 300 of FIG. 5 with a two-piece collar 130 attached thereto via a fixation screw 400. To locate a second implant hole with respect to the first, previously installed, implant 300, a connective stem 200 with a bar portion 210 of the appropriate length to provide the desired center-to-center spacing between implants is selected by the dental surgeon. One end portion 205 of the connective stem 200 is press-fit into the side socket 138 of the collar 130, and the opposing end portion 215 of the connective stem 200 is slid downwardly in the channel 960 of the drill sleeve 950 where it is captured by narrowed opening 912, thereby joining the drill sleeve 950 to the implant 300. A drill bit 50 is placed through the bore 955 of the drill sleeve 950, and a new implant hole is drilled therethrough. Then the drill bit 50 and drill sleeve 950 are removed to install another implant and modular collar in the second implant hole, such as the implant 300 and the collar 130, for example.

In yet another aspect, preferred embodiments of the present invention comprise an improved procedure for installing a multi-unit prosthetic restoration. In particular, one preferred embodiment of the improved procedure comprises a method of drilling properly spaced and parallel implant holes, installing the implants in the drilled holes, fabricating a dental framework system directly onto the implants in the dental surgeon's office, and attaching a multi-unit prosthetic restoration to the framework, all in a single surgical setting. As used herein, the phrase "single surgical setting" when used to describe the timing associated with performing various procedures or steps means that all such steps are performed during a single visit to the office of the dental professional, as contrasted with performing those steps over multiple visits by the patient over various days, weeks or months.

In more detail, one preferred embodiment of the procedure comprises taking an impression of the patient's edentulous ridge from which a cast model of the patient's arch is made. Using the model and other diagnostic information, the dental surgeon can determine the location and angular orientation of each implant, determine which prefabricated framework components of the present system will be used, and fabricate the prosthetic restoration that will be installed. On the day of surgery, the implant holes will be drilled as planned, preferably utilizing the drill guide components and methods heretofore described with respect to FIGS. 13, 14 and 18. The implants will then be installed. Then the framework will be installed, preferably utilizing the prefabricated modular collars and connective members of the preferred embodiments of the present invention. Accordingly, the framework will be installed, component by component, in the dentist's office in the same surgical setting as the implants.

Referring again to FIG. 15, an isometric view is shown of one exemplary implant and framework system for a full prosthetic lower arch comprising four implants 700, with modular collars 100, 150 connected via fixation screws 400 to the implants 700. Further, the modular collars 100, 150 are connected to one another via connective stems 200 having bar portions 210 that span the space therebetween. As previously disclosed, in order to best depict how the implants 700 and collars 100, 150 fit together, the collars 100, 150 are shown displaced from the implants 700. However, when the framework system is installed, the lower portions 112, 162 of collars 100, 150 will fit into the upper recesses 710 of the implants 700 to mount the collars 100, 150 directly atop the implants 700, and the fixation screws 400 will be fully threaded into the implants 700.

Once the implants 700 and framework system are installed, the prosthetic denture can be attached to the framework. Preferably, the denture would include attachment recesses for receiving the bar portions 210 of the connective stems 200a, 200b, 200c, thereby enabling the denture to snap into place onto the framework system. Optionally, the denture may include attachment extensions matching the position and size of the optional top recesses 110, 160 of the modular collars 100, 150 to provide an additional means for securing the denture to the framework system. The denture preferably further includes two sockets at the very back of the arch matching the position and size of the attachment portions 265 of the connective elbows 250, thereby enabling the denture to snap into place at this location.

This method of installing the implants, framework, and prosthetic restoration in the same surgical setting will obviously result in immediate loading on the implant-supported denture since no delay is provided to allow the implants to osseo-integrate into the jawbone. Conventionally, a delay of 1-6 months is provided for osse-integration of the implants into the jawbone. However, immediate loading is now advocated by a number of dental surgeons and dental prosthetic companies as a condition that is beneficial to osseo-integration. Accordingly, as immediate loading becomes a more accepted and more widespread practice, the above-described single surgical setting procedure will be beneficial for reducing time, cost, and inconvenience to the patient.

Another embodiment of the present invention comprises an improved procedure for installing a multi-unit prosthetic restoration without immediate loading. The procedure for installing the implants and framework system would preferably be the same as previously described, i.e. the implants and framework system would be installed in the same surgical setting. Following installation of the framework system, such as that shown in FIG. 15, another impression would be made of the patient's edentulous ridge, this time with the implants and framework system installed. Another model of the patient's arch would be made from this impression, from which the prosthetic restoration would be built. Utilizing this procedure, the patient would wear a temporary, removable denture while the permanent denture was being built, and the framework could either remain in the patient's mouth during that period, or it could be removed and reinstalled at the time when the permanent denture is attached.

Accordingly, in one aspect, the preferred embodiments of the present invention comprise a group of inter-connecting, prefabricated, preferably titanium components of various shapes and sizes that can be assembled together to form a framework system directly onto implants installed in the patient's mouth. Thus, the framework can be fabricated on site in the dental surgeon's office in a single surgical setting so that multiple trips back and forth to the surgeon's office and/or dental laboratory are eliminated. Further, no intra-oral welding is required, nor adjustment of system components, such as by cutting connective members to fit.

In another aspect, the preferred embodiments of the present invention comprise a group of inter-connecting, prefabricated components to form a drill guide system for drilling an implant hole adjacent to another implant hole or adjacent to a fully-installed implant. Namely, the drill guide system previously described enables implants to be drilled at the proper distance and in a parallel relationship to adjacent implants. Further, none of the drill guide system components are custom-made, nor are they destroyed during use, such that they can preferably be utilized more than once, for any configuration of restoration, and on any patient.

In yet another aspect, the preferred embodiments of the present invention comprise improved procedures for installing permanent, implant-supported dental restorations. If the doctor believes immediate loading is preferred, then using a model of the patient's arch, the implants can be located, the framework can be designed, and the denture prosthesis can be pre-fabricated—all in advance. Accordingly, when the patient arrives on the day of dental surgery, the implants can be installed, the framework constructed and attached to the implants, and the denture fixed to the framework, such that the entire installation is completed in a single surgical setting.

Further, if the doctor does not believe that immediate loading is preferred, the procedure of the preferred embodiments still provides time and cost-saving advantages because the framework need not be custom-built in a laboratory, but instead can be constructed and installed in the same surgical setting in which the implants are surgically implanted. Then an impression of the installed implants and/or framework can be made to form a model from which the dental prosthesis can be built for installation after the osseo-integration period.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims that follow, the scope of which shall include all equivalents of the subject matter of the claims.

What is claimed is:

1. Apparatus to fabricate an intraoral framework that attaches to surgically installed dental implants, said apparatus comprising:
   a first connective node having a body comprising a proximal surface, a pair of side surfaces, a pair of end surfaces, and a generally flat distal surface;
   a socket formed in each of said end surfaces of said body;
   said proximal surface of said body having an extending portion adapted to fit within a recess formed in an installed implant;
   a throughbore with a central axis formed through said body and passing through said distal surface and through said extending portion of said proximal surface.

2. The apparatus of claim 1 wherein said body is symmetrical about a plane of symmetry that contains said central axis of said throughbore, and wherein said sockets each include a bore having a central axis.

3. The apparatus of claim 2 wherein said axes of said socket bores lie within the same plane and are coaxially aligned.

4. The apparatus of claim 3 wherein said distal surface is generally rectangular.

5. The apparatus of claim 2 wherein said axes of said socket bores lie within the same plane and intersect one another at an angle less than 180 degrees.

6. The apparatus of claim 5 wherein at least one of said side surfaces includes two generally planar surfaces that are not coplanar with each other and that intersect one another at said plane of symmetry.

7. The apparatus of claim 5 wherein said axes of said socket bores intersect one another at an angle of between 100 and 170 degrees.

8. The apparatus of claim 2 further comprising a connective framework member having first and second end portions that each includes a surface having a spherical radius, and wherein said first end portion is disposed in one of said sockets of said first connective node.

9. The apparatus of claim 8 further comprising a second connective node having a first end surface and a first socket formed therein, and wherein said second end portion of said connective framework member is disposed in said first socket of said second connective node.

10. The apparatus of claim 9 further comprising an elbow shaped connective framework member having first and second end portions that each includes a surface having a spherical radius, and wherein said second connective node includes a second end surface having a second socket formed therein, and wherein a first end portion of said elbow shaped connective framework member is disposed in said second socket of said second connective node.

11. The apparatus of claim 9 wherein at least one of said first and second end portions of said connective framework member is disposed within a bushing.

12. The apparatus of claim 11 wherein said bushing comprises a spherical recess.

13. The apparatus of claim 11 wherein said bushing comprises a cylindrical recess.

14. The apparatus of claim 8 wherein said connective framework member is generally L-shaped.

15. The apparatus of claim 14 wherein said spherical radius of said second end portion is larger than the spherical radius of said first end portion.

16. A system of prefabricated framework components for joining at least two dental implants, comprising:
 a first collar and a second collar;
 a connective stem configured to be attachable to the first collar and the second collar comprising a unitary bar portion having a first enlarged portion on a first end and a second enlarged portion on a second end;
 wherein the first enlarged portion is received within the first collar and the second enlarged portion is received within the second collar, said unitary bar portion extending uninterrupted between said collars thereby connecting the first collar to the second collar.

17. The system of claim 16 further comprising at least one connective elbow having an end portion thereof received within one of said first collar or said second collar.

18. The system of claim 17 wherein said connective elbow comprises an elbow portion, an enlarged portion, and an attachment portion.

19. The system of claim 18 wherein said enlarged portion is adapted to connect to said first or said second collar, and said attachment portion is adapted for attaching a prosthetic restoration thereto.

20. The system of claim 16 wherein at least one of said first collar or said second collar is a two-piece member.

21. The system of claim 16 wherein at least one of said first collar or said second collar has a distal and a proximal surface, and wherein said distal surface is generally rectangular in shape.

22. The system of claim 16 wherein at least one of said first collar or said second collar has two symmetrical portions angled with respect to one another.

23. The system of claim 16 wherein each of said first collar and said second collar comprises a body having a recess formed in its distal surface for attaching a prosthetic restoration thereto.

24. The system of claim 16 wherein each of said first collar and said second collar comprises a body having at least two side sockets.

25. The system of claim 16 wherein each of said first collar and said second collar has an extension portion adapted for direct engagement with an implant.

26. The system of claim 16 further comprising an interface conversion piece adapted to connect a collar to a sub-gingival implant.

27. The system of claim 16 wherein each of said first collar and said second collar has a recessed portion adapted for receiving an extension portion of an implant.

28. The system of claim 16 wherein at least one of said enlarged portions is received within a bushing disposed in one of said first collar or said second collar.

29. The system of claim 28 wherein said bushing comprises a spherical recess.

30. The system of claim 28 wherein said bushing comprises a cylindrical recess.

31. A method of installing a dental prosthetic comprising:
 drilling at least two implant holes during a first surgical setting;
 installing an implant in each implant hole during the same surgical setting;
 assembling a framework directly onto the implants during the same surgical setting,
wherein the assembling step comprises attaching a connective stem to a first collar and a second collar, wherein the connective stem has a first enlarged portion on a first end and a second enlarged portion on a second end and wherein the first enlarged portion is received within the first collar and the second enlarged portion is received within the second collar; and
 attaching the dental prosthetic to the framework;
 wherein the framework is assembled with intra-oral welding.

32. The method of claim 31 wherein the dental prosthetic is attached to the framework during the same surgical setting.

33. The method of claim 31 wherein the dental prosthetic is attached to the framework after an osseo-integration period.

34. The method of claim 31 wherein the framework is assembled from prefabricated components of predetermined lengths that interconnect and require no cutting to assemble into the framework.

* * * * *